(12) United States Patent
Gonzalez Trotter et al.

(10) Patent No.: US 6,748,047 B2
(45) Date of Patent: Jun. 8, 2004

(54) SCATTER CORRECTION METHOD FOR NON-STATIONARY X-RAY ACQUISITIONS

(75) Inventors: Dinko Eduardo Gonzalez Trotter, Clifton Park, NY (US); Serge Louis Muller, Guyancourt (FR)

(73) Assignee: General Electric Company, Schenectady, NY (US)

( * ) Notice: Subject to any disclaimer, the term of this patent is extended or adjusted under 35 U.S.C. 154(b) by 70 days.

(21) Appl. No.: 10/063,806

(22) Filed: May 15, 2002

(65) Prior Publication Data

US 2003/0215057 A1 Nov. 20, 2003

(51) Int. Cl.[7] .......................................... G01N 23/083
(52) U.S. Cl. ..................................... 378/62; 378/98.4
(58) Field of Search ........................... 378/4, 7, 15, 62, 378/98.4, 901

(56) References Cited

U.S. PATENT DOCUMENTS

| | | |
|---|---|---|
| 3,971,950 A | 7/1976 | Evans et al. |
| 4,407,163 A | 10/1983 | Hundt et al. |
| 4,509,368 A | 4/1985 | Whiting et al. |
| 4,543,959 A | 10/1985 | Sepponen |
| 4,936,291 A | 6/1990 | Forssmann et al. |
| 5,361,767 A | 11/1994 | Yukov |
| 5,474,072 A | 12/1995 | Shmulewitz |
| 5,479,927 A | 1/1996 | Shmulewitz |
| 5,603,326 A | 2/1997 | Richter |
| 5,630,426 A | 5/1997 | Eggers et al. |
| 5,640,956 A | 6/1997 | Getzinger et al. |
| 5,660,185 A | 8/1997 | Shmulewitz et al. |
| 5,664,573 A | 9/1997 | Shmulewitz |
| 5,735,264 A | 4/1998 | Siczek et al. |
| 5,776,062 A | 7/1998 | Nields |
| 5,803,082 A | 9/1998 | Stapleton et al. |
| 5,810,742 A | 9/1998 | Pearlman |
| 5,820,552 A | 10/1998 | Crosby et al. |
| 5,828,774 A | 10/1998 | Wang |
| 5,840,022 A | 11/1998 | Richter |
| 5,851,180 A | 12/1998 | Crosby et al. |
| 5,855,554 A | 1/1999 | Schneider et al. |
| 5,872,828 A | 2/1999 | Niklason et al. |
| 5,923,775 A | 7/1999 | Snyder et al. |
| 5,938,613 A | 8/1999 | Shmulewitz |
| 5,983,123 A | 11/1999 | Shmulewitz |
| 5,984,870 A | 11/1999 | Giger et al. |
| 5,999,639 A | 12/1999 | Rogers et al. |
| 6,180,943 B1 | 1/2001 | Lange |
| 6,590,213 B2 * | 7/2003 | Wollenweber ......... 250/363.03 |
| 2003/0047687 A1 * | 3/2003 | Wollenweber ......... 250/363.03 |
| 2003/0138074 A1 * | 7/2003 | Bruder ........................ 378/4 |

OTHER PUBLICATIONS

A. Thomas Stavros et al.: "Solid Breast Nodules: Use of Sonography to Distinguish between Benign and Malignant Lesions," Radiology, Jul. 1995, pp. 123–134, vol. 196, No. 1, Englewood, CO.

Thomas M. Kolb et al.: "Occult Cancer in Women with Dense Breasts: Detection with Screening US–Diagnostic Yield and Tumor Characteristics," Radiology, Apr. 1998, pp. 191–199, vol. 207, No. 1.

(List continued on next page.)

Primary Examiner—David V Bruce
(74) Attorney, Agent, or Firm—Foley & Lardner

(57) ABSTRACT

A method of estimating an asymmetrical scatter signal distribution wherein asymmetry is introduced by angular incidence of radiation, which has been emitted from a source and transmitted through an object to be imaged, on a detector, is disclosed. This method includes, in an embodiment, modifying scatter that would be derived wherein the radiation is directly incident on the detector with zero degrees of inclination, using an asymmetry factor which indicates the shape and magnitude of the scatter signal distribution and which varies with an angle at which the radiation is incident on the detector, a mean attenuation coefficient of the object, and a distance the radiation has traveled through the object. The estimated scatter provides for correction of scatter in a image.

24 Claims, 10 Drawing Sheets

OTHER PUBLICATIONS

Daniel B. Kopans et al.: "Development and Clinical Evaluation of Tomosynthesis for Digital Mammography; Technical and Cost Proposal," Clinical Translational Research Award, Department of Defense Breast Cancer Research Program, Nov. 19, 1997, pp. 1–54.

Nico Karssemeijer: "Computer–Aided Detection and Interpretation in Mammography," pp. 243–252.

Nico Karssemeijer et al.: "Detection of Stellate Distortions in Mammograms," IEEE Transactions on Medical Imaging, Oct. 1996, pp. 611–619, vol. 15, No. 5, IEEE.

Ioanna Christoyianni et al.: "Fast Detection of Masses in Computer–Aided Mammography," IEEE Signal Processing Magazine, Jan. 2000, pp. 54–64.

Celia Byrne et al.: "Mammographic Features and Breast Cancer Risk: Effects with Time, Age, and Menopause Status," Journal of the National Cancer Institute, Nov. 1, 1995, pp. 1622–1629, vol. 87, No. 21.

Milan Sonka et al.: "Computer–Aided Diagnosis in Mammography," Handbook of Medical Imaging—vol. 2. Medical Image Processing and Analysis, pp. 915–958, Spie Press, Bellingham, Washington.

Matthew A. Kupinski et al.: "Feature Selection and Classifiers for the Computerized Detection of Mass Lesions in Digital Mammography," IEEE Int. Conf. On Neural Nets, 1997, pp. 2460–2463, IEEE.

Shuk–Mei Lai et al.: "On Techniques for Detecting Circumscribed Masses in Mammograms," IEEE Transactions on Medical Imaging, Dec. 1989, pp. 377–386, vol. 8, No. 4, IEEE.

Marios A. Gavrielides et al.: "Segmentation of Suspicious Clustered Microcalcifications in Mammograms," Med. Phys., Jan. 2000, pp. 13–22, vol. 27, No. 1, Am. Assoc. Phys. Med.

Weizhang et al.: "Optimally Weighted Wavelet Transform Based on Supervised Training for Detection of Microcalcifications in Digital Mammograms," Med. Phys. Jun. 1998, pp. 949–956, vol. 25, No. 6, Am. Assoc. Phys. Med.

Berkman Sahiner et al.: "Computerized Characterization of Masses on Mammograms: The Rubber Band Straightening Transform and Texture Analysis," Med. Phys. Apr. 1998, pp. 516–526, vol. 25, No. 4, Am. Assoc. Phys. Med.

Zhimin Huo et al.: "Computerized Analysis of Mammographic Parenchymal Patterns for Breast Cancer Risk Assessment: Feature Selection," Med. Phys., Jan. 2000, pp. 4–12, vol. 27, No. 1, Am. Assoc. Phys. Med.

Datong Wei et al.: "Classification of Mass and Normal Breast Tissue on Digital Mammograms: Multiresolution Texture Analysis," Med. Phys. Sep. 1995, pp. 1501–1513, vol. 22, No. 9, Am. Assoc. Phys. Med.

John J. Heine et al.: "Multiresolution Statistical Analysis of High–Resolution Digital Mammograms," IEEE Transactions on Medical Imaging, Oct. 1997, pp. 503–515, vol. 16, No. 5, IEEE.

Wouter J. H. Veldkamp et al.: Normalization of Local Contrast in Mammograms, IEEE Transaction on Medical Imaging, Jul. 2000, pp. 731–738, vol. 19, No. 7, IEEE.

Wei Qian et al.: "Tree Structured Wavelet Transform Segmentation of Microcalcifications in Digital Mammography," Med. Phys., Aug. 1995, pp. 1247–1254, vol. 22, No. 8, Am. Assoc. Phys. Med.

Highnam et al.: "Mammographic Image Analysis," 1999, pp. 39–53, 191–223, 288, Kluwer Academic Publishers.

Duda et al.: "Pattern Classification," 2001, pp. 161–199.

Laura M. Yarusso et al.: "Application of Computer–Aided Diagnosis to Full–Field Digital Mammography," IWDM 2000, $5^{th}$ International Workshop on Digital Mammography, pp. 421–246, 2001, Medical Physics Publishing, Madison, Wisconsin.

Lihua Li et al.: "Hybrid Classification Method for False–Positive Reduction in CAD for Mass Detection," IWDM 2000, $5^{th}$ International Workshop on Digital Mammography, pp. 272–279, 2001, Medical Physics Publishing, Madison, Wisconsin.

Robert P. Velthuizen: "Computer Description of Mammographic Masses," IWDM 2000, $5^{th}$ International Workshop on Digital Mammography, pp. 395–401, 2001, Medical Physics Publishing, Madison, Wisconsin.

Armando Bazzani et al.: "Automatic Detection of Clustered Microcalcifications Using a Combined Method and an SVM Classifier," IWDM 2000, $5^{th}$ International Workshop on Digital Mammography, pp. 161–167, 2001, Medical Physics Publishing, Madison, Wisconsin.

Yoshihiro Hagihara et al.: "Accurate Detection of Microcalcifications on Mammograms by Improvement of Morphological Processing," IWDM 2000, $5^{th}$ International Workshop on Digital Mammography, pp. 193–197, 2001, Medical Physics Publishing, Madison, Wisconsin.

M. Lanyi: "Diagnosis and Differential Diagnosis of Microcalcifications," Ductal Carcinomas of Varying Histologic Types, pp. 44, 60, 61, 86, 95, 98–101, 110, 118–120, and 192, 1987, Springer–Verlag.

Daniel B. Kopans: "The Positive Predictive Value of Mammography," AJR, Mar. 1992, pp. 521–526, vol. 158, American Roentgen Ray Society.

J. A. Seibert "X–ray Scatter Removal by Deconvolution" pp. 567–575, 1988 Am. Assoc. Phys. Med.

Dinko E. Gonzalez Trotter Thickness–dependent Scatter Correction Algorithm for Digital Mammography.

John J. Heine, Mammographic Tissue, Breast Cancer Risk, Serial Image Analysis, and Digital Mammography, Part 1, Academic Radiology, vol. 9, pp. 298–316, No. 3, Mar. 2002.

John J. Heine, Mammographic Tissue, Breast Cancer Risk, Serial Image Analysis, and Digital Mammography, Part 2, Academic Radiology, vol. 9, No. 3, pp. 317–335, Mar. 2002.

John M. Boone "Scatter/Primary in Mammography: Comprehensive Results" pp. 2408–2416, 2000 Am. Assoc. Phys. Med.

* cited by examiner

---- $y_k$ (20 deg)
□ $b_k$ (20 deg)
—— $b'_k$ (20 deg)

SCATTER CORRECTION METHOD FOR NON-STATIONARY X-RAY ACQUISITIONS

STATEMENT REGARDING FEDERALLY SPONSORED RESEARCH & DEVELOPMENT

The government may have rights in this invention pursuant to Subcontract MDA 905 001 0041 issued from the Office of Naval Research/Henry M. Jackson Foundation.

BACKGROUND OF THE INVENTION

The present invention relates generally to scatter-correction for X-ray or the like type of examination technique, and more specifically to a scatter-correction technique for situations wherein the angle of incidence of an incident ray from a radiation source impinges on a detector at an angle which is not exactly zero degrees or exactly at right angles to the detector, and thus allows for the source to be moved with respect to the detector or vice versa.

Breast cancer is a significant cause of mortality among women in the United States. Currently the most widespread breast-cancer screening technique is X-ray mammography, where malignancies are detected based on their characteristic shape (typically spiculated) and radiological density (similar to breast glandular tissue).

Early detection of breast cancer generally improves a patient's chance of survival and is thus of critical importance. The task of detection of malignancies is complicated by the fact that the breast is a radiologically complex 3D structure that is imaged by 2D X-ray projection. Thus, malignant lesions can be masked by surrounding glandular tissue, decreasing contrast and distorting the lesion's perceived shape. A significant number of malignancies are missed in mammography because of the presence of this increase of structural noise brought about by the projection of 3D structures in the breast onto a 2D image.

Tomosynthesis is a promising alternative to conventional two-dimensional mammography. This imaging technique resides in the acquisition of plural low-dose 2D X-ray projection images, where the X-ray source is moved along an arcuate trajectory with respect to the stationary breast and/or detector. X-ray projections are thus acquired at different angles. These angular projections are then combined in a 3D image reconstruction of the breast. In the reconstructed image, the overlap of 3D structures is mitigated, contrast is enhanced and the morphological features of malignancies (speculation) can be better preserved than in 2D X-ray imaging, therefore leading to improved sensitivity and specificity with respect to 2D X-ray mammography.

In tomosynthesis, the use of a non-stationary X-ray source precludes the use of a traditional grid for scatter rejection. With larger source angles with respect to the detector normal, the scatter signal will increase due to the longer distances that the X-rays traverse through the breast tissue. Therefore, there is a need to be able to estimate the scatter component on an X-ray image that has been acquired and compensate for the scattering in order to improve the resolution/effectiveness of the examination of the breast tissue.

BRIEF SUMMARY OF THE INVENTION

More specifically, a first aspect of the present invention resides in a method of estimating scatter in an image, where radiation from a radiation source is transmitted through an object to be imaged and is incident on a detector at an inclined or "non-zero" angle. This method comprises explicitly modeling an effect of angular incidence of the radiation on a scatter signal, including deriving, using an empirically based correction which includes the effect of a non-zero angle of incidence of the radiation on the detector, an estimate of the scatter signal in image data derived from the incident radiation on the detector.

A second aspect of the invention resides in a method of calculating and removing scatter from an image, where radiation emitted from a source is transmitted through an imaged object, is incident on a detector at a non-zero (acute) angle, comprising: explicitly modeling the effect of angular incidence of radiation in a scatter signal; re-normalizing the scatter signal depending on the angle of incidence of radiation and the thickness of the object imaged; and correction of scatter from an image based on inverse-filtering.

A third aspect of the invention resides in a method of estimating scatter in an X-ray image, where radiation emitted from an X-ray source is transmitted through an imaged object and is incident on the X-ray detector at an acute or non-zero angle, comprising: explicitly modeling the effect of angular incidence of X-ray radiation in a scatter signal; and calculating, via convolution, an estimate of the scatter signal in an X-ray image.

A fourth aspect of the invention resides in a method of estimating an asymmetrical scatter kernel wherein asymmetry is introduced by angular incidence of radiation, which has been emitted from a source and transmitted through an object to be imaged, on a detector, comprising: modifying scatter that would be derived wherein the radiation is directly incident on the detector with zero degrees of inclination, using an asymmetry factor which indicates the shape and magnitude of the scatter kernel and which varies with an angle at which the radiation is incident on the detector, a mean attenuation coefficient of the object, and a distance the radiation has traveled through the object.

Further aspects of the invention respectively reside in computer readable media which are encoded with programs executable by a computer for implementing the above mentioned methods. Additionally imaging systems which include hardware and computer software and which are adapted to implement the above mentioned methods, also comprise further aspect of the invention.

BRIEF DESCRIPTION OF THE DRAWINGS

FIG. 11 shows, after scatter correction, the percent deviation between the scatter-free signal and the scatter corrected signal within the 5 cm breast phantom (25° acquisition).

DETAILED DESCRIPTION OF THE PREFERRED EMBODIMENTS

The present invention is directed to a scatter-correction technique which enables the angle of the incident radiation to be taken into account and thus includes the relative position between the radiation source and the radiation detector arrangement which receives the radiation in the calculation and correction for scatter. It will be noted that the angle of incidence can very closely approach zero degrees (viz., exactly parallel to the normal of the detector plane and thus effectively encompass all angles which are encountered and in which scattering occurs and needs to be either determined and/or corrected for.

Before dealing with the concept on which the present invention is based, it is appropriate to consider an example of the type of device to which the concept of the invention can be applied.

Figure 1:
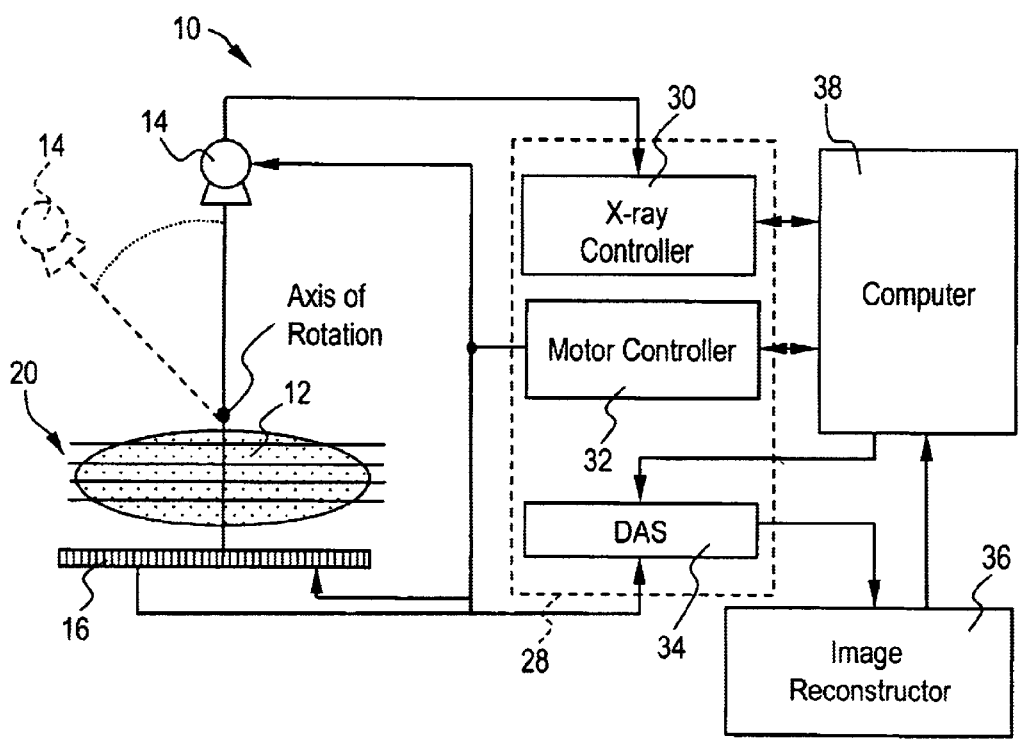
FIG. 1 is a schematic representation of an example of an X-ray system that the embodiments of the present invention can be applied.

FIG. 1 is a schematic representation of an imaging system 10, such as conventionally used in X-ray mammography imaging and tomosynthesis imaging. This system 10 includes at least one radiation source 14, such as an X-ray source, and at least one detector array 16 for receiving radiation emitted from the radiation source at one or more projection angles. This system can be adapted, for example, so that the radiation source 14 projects a cone-shaped beam of X-rays which pass through object 12 and impinge on the detector array 16.

The detector array 16 has a plurality of detector elements (not shown per se) arranged in rows and columns such that image data of the object 12 of interest can be suitably collected. As is conventional the detector elements can each comprise one or more photosensors, such as photodiodes. The radiation which is incident on a scintillator material enables the photosensors to measure, by way of change in the charge across the diode(s), an amount of light generated by X-ray interaction with the scintillator.

Simply byway of explanation, the operation of radiation source 14 is governed by a control mechanism 28 of the imaging system 10. This control mechanism 28 includes a radiation controller 30 that provides power and timing signals to the radiation source 14 and a motor controller 32 that controls a respective movement speed and position of radiation source 14 and detector array 16.

A data acquisition system (DAS) 34 which is included in the control mechanism 28 samples digital data from detector 16 for subsequent processing. An image processor 36 receives a sampled and digitized projection data set from DAS 34 and performs image processing and scatter correction, as described herein. A system controller 38, such as a computer or a microprocessor control the other elements of the system 10.

Figure 2:
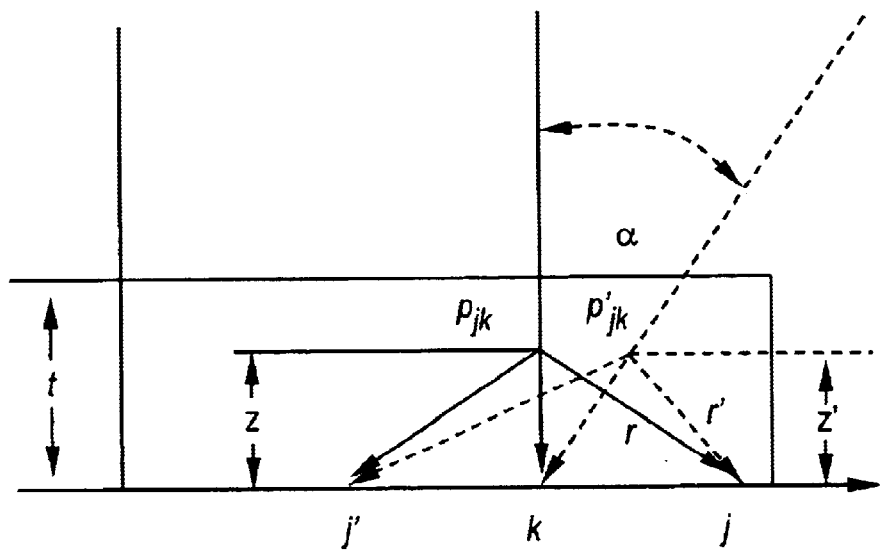
FIG. 2 is a diagram which depicts the foundation of equations 1–14.
Figure 3:
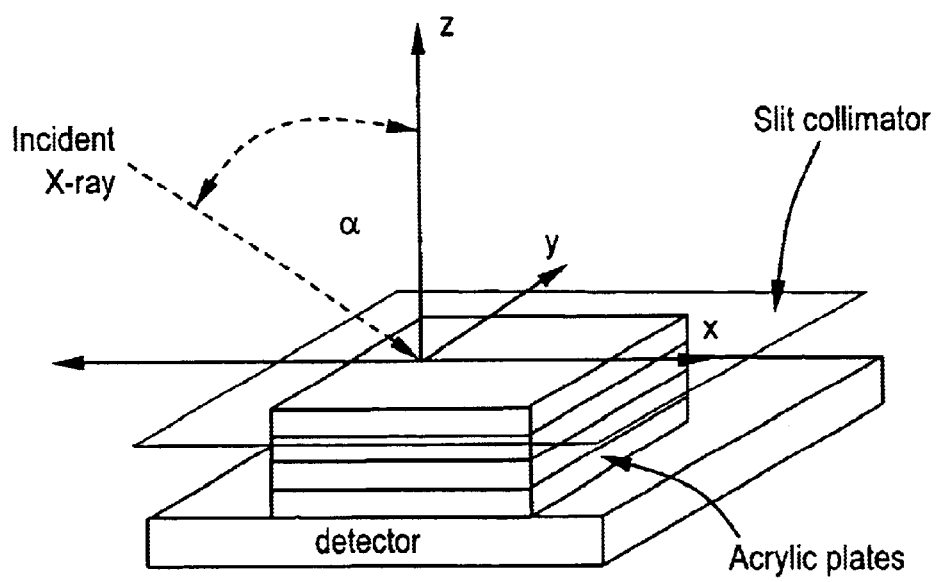
FIG. 3 is a schematic perspective view showing an experimental setup for angular measurements of scattered radiation.
Figure 4:
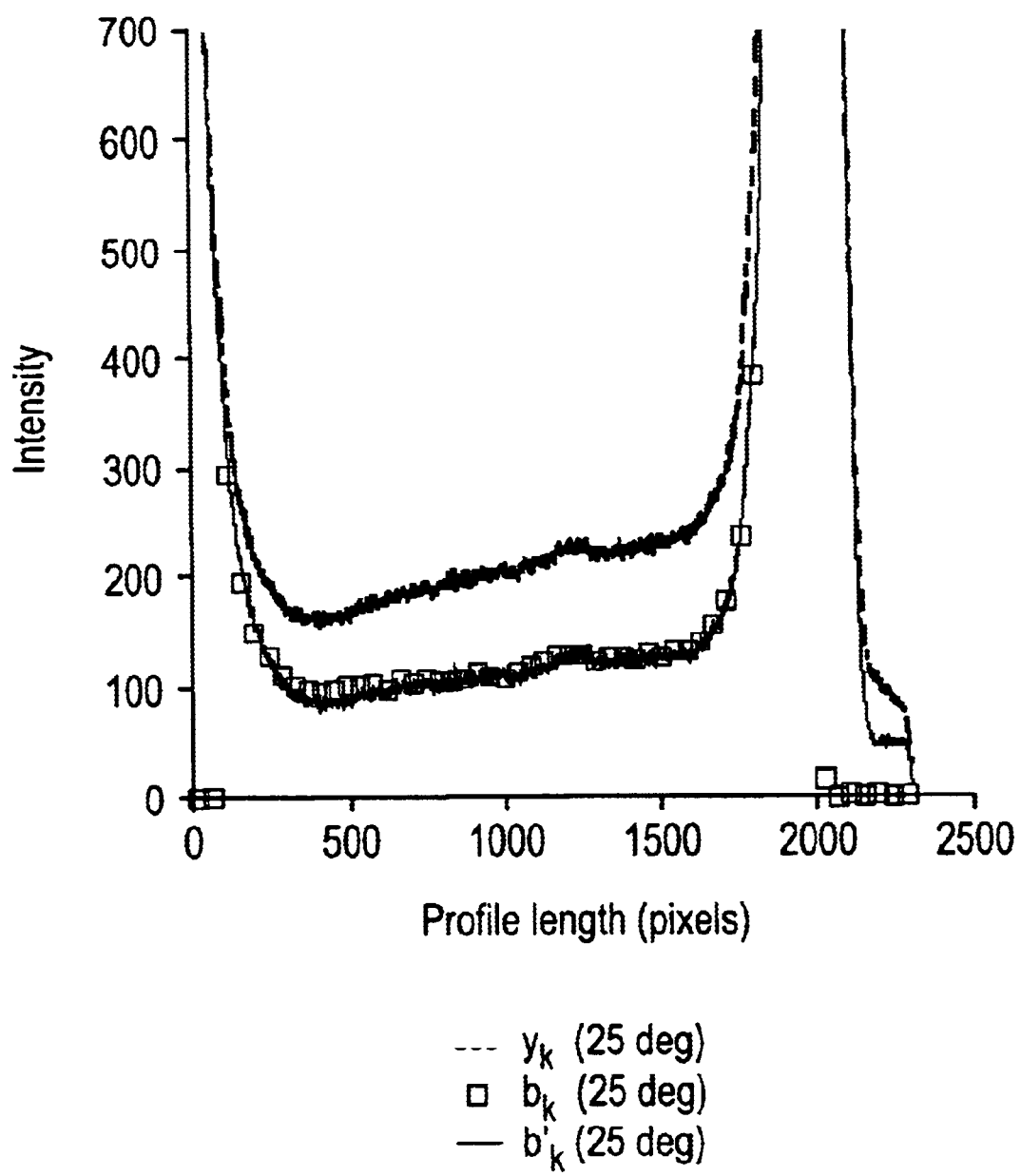
FIGS. 4–9 are graphical comparison between open-geometry ($y_k$), scatter-free ($b_k$) and scatter-corrected ($b'_k$) signals for a 25° angular acquisition.
Figure 5:
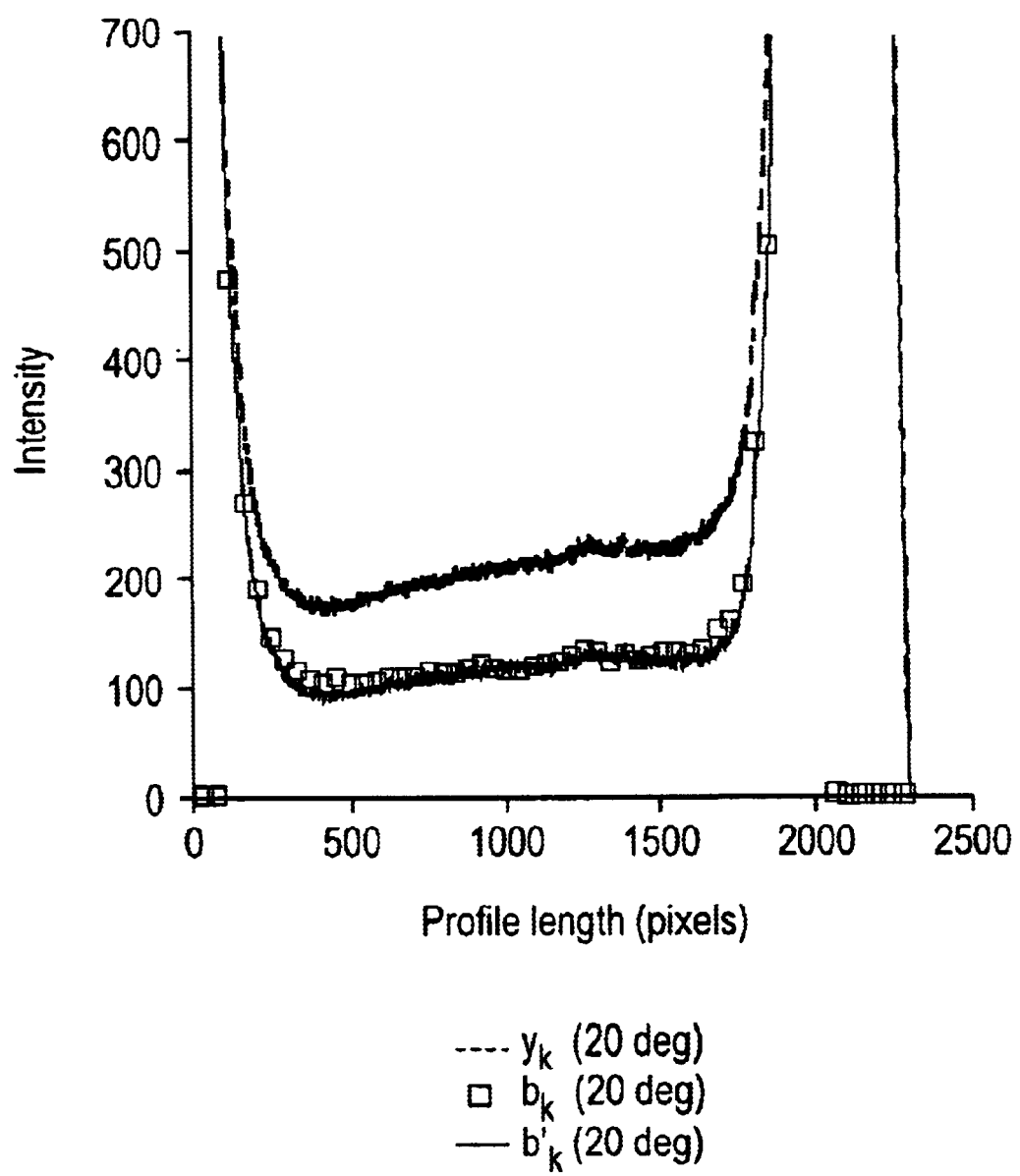
Figure 6:
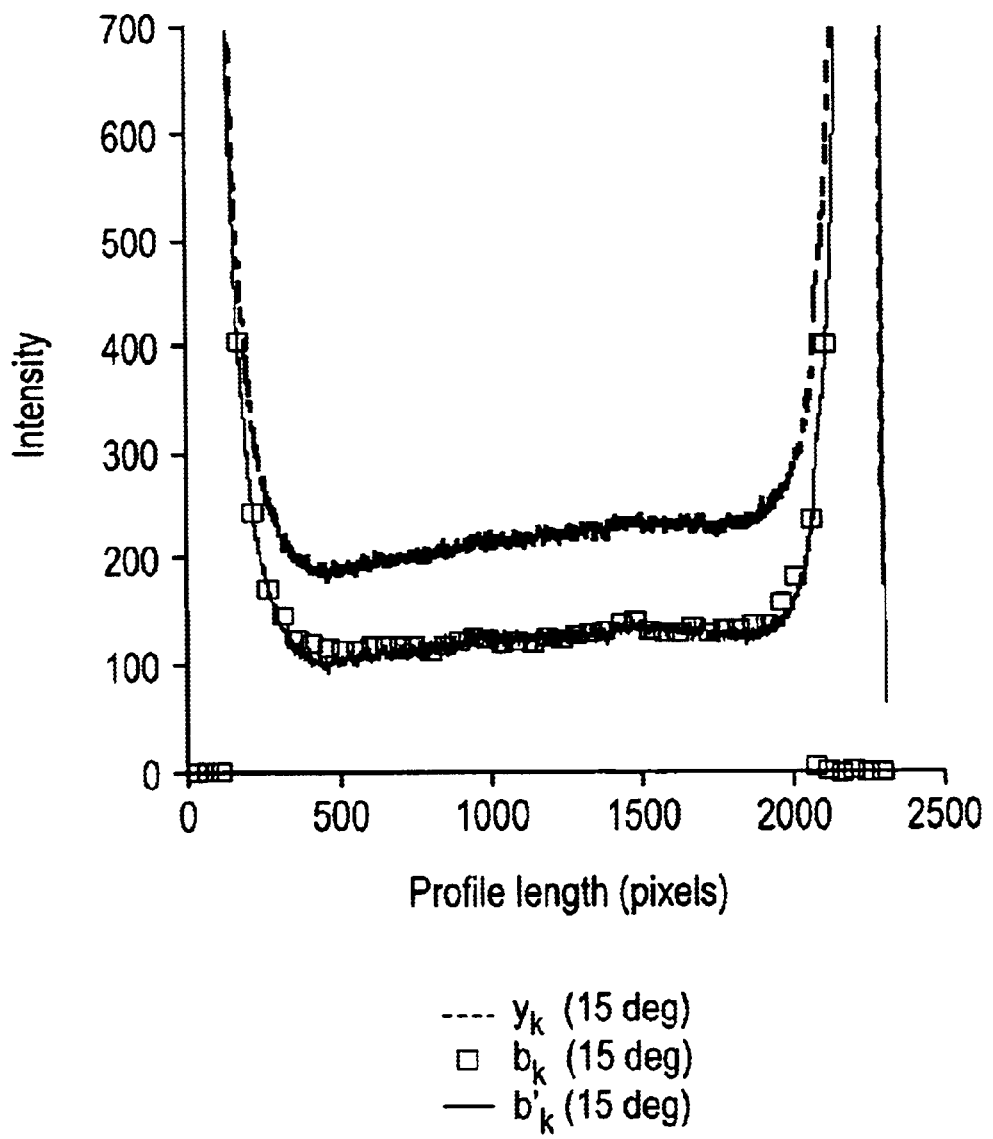
Figure 7:
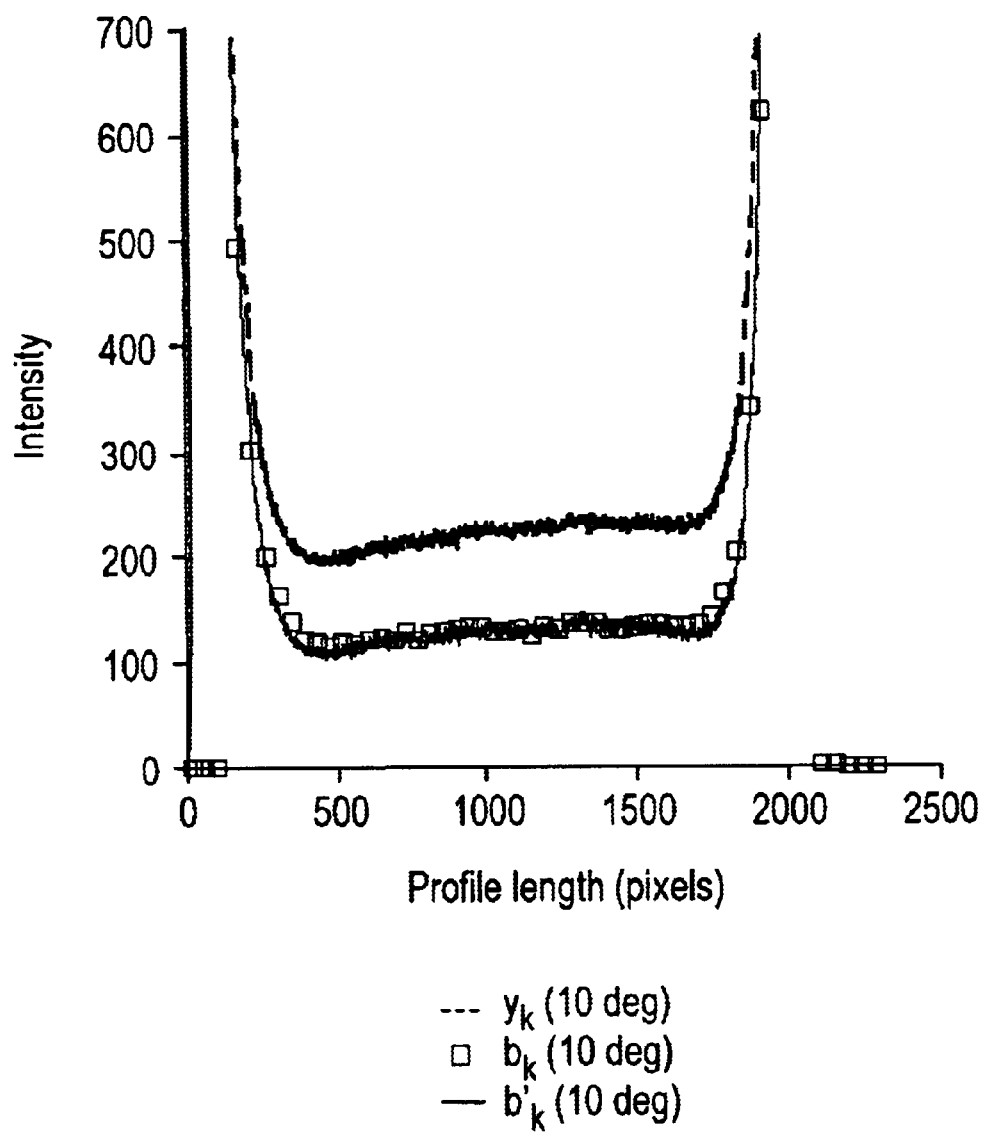
Figure 8:
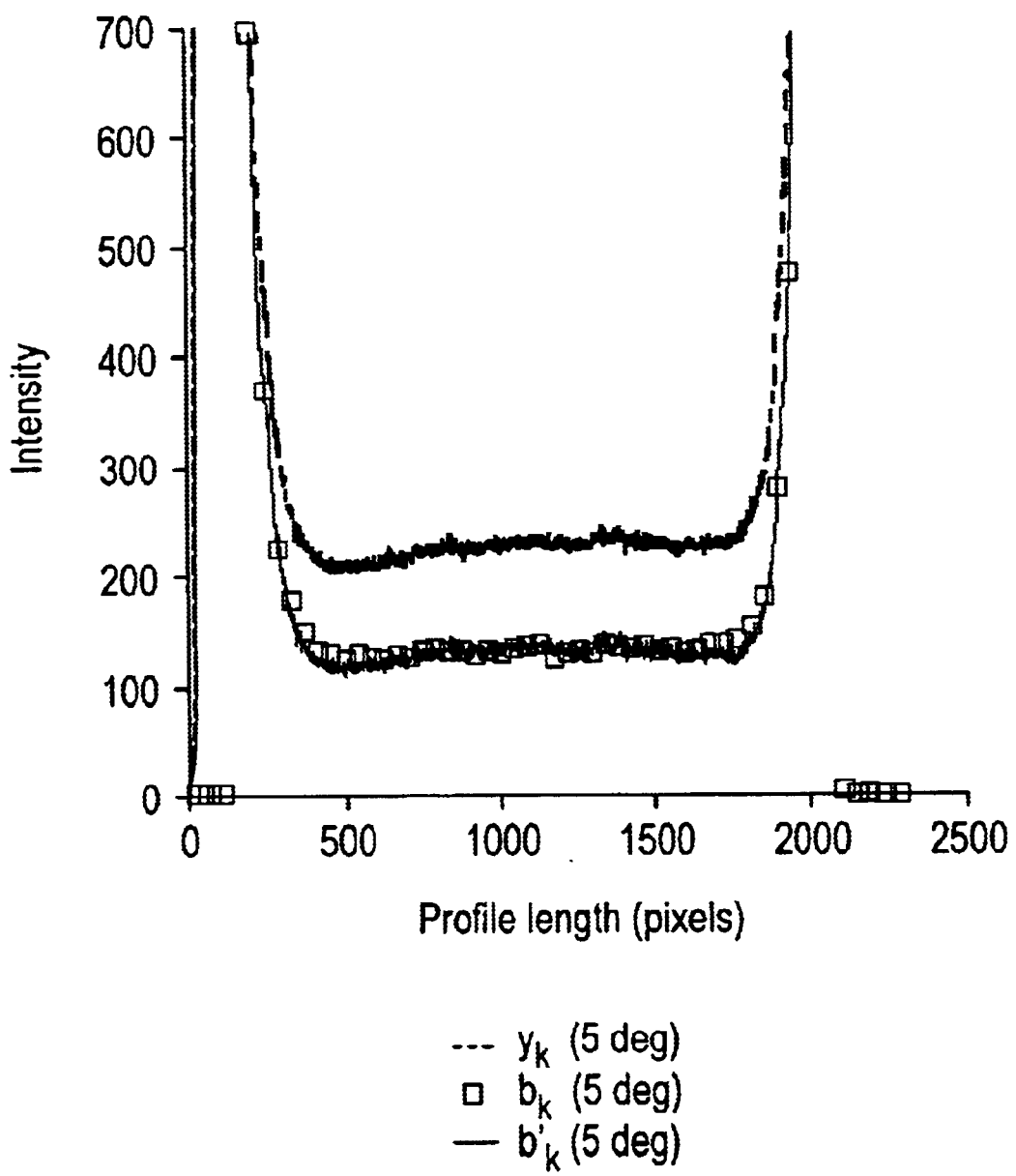
Figure 9:
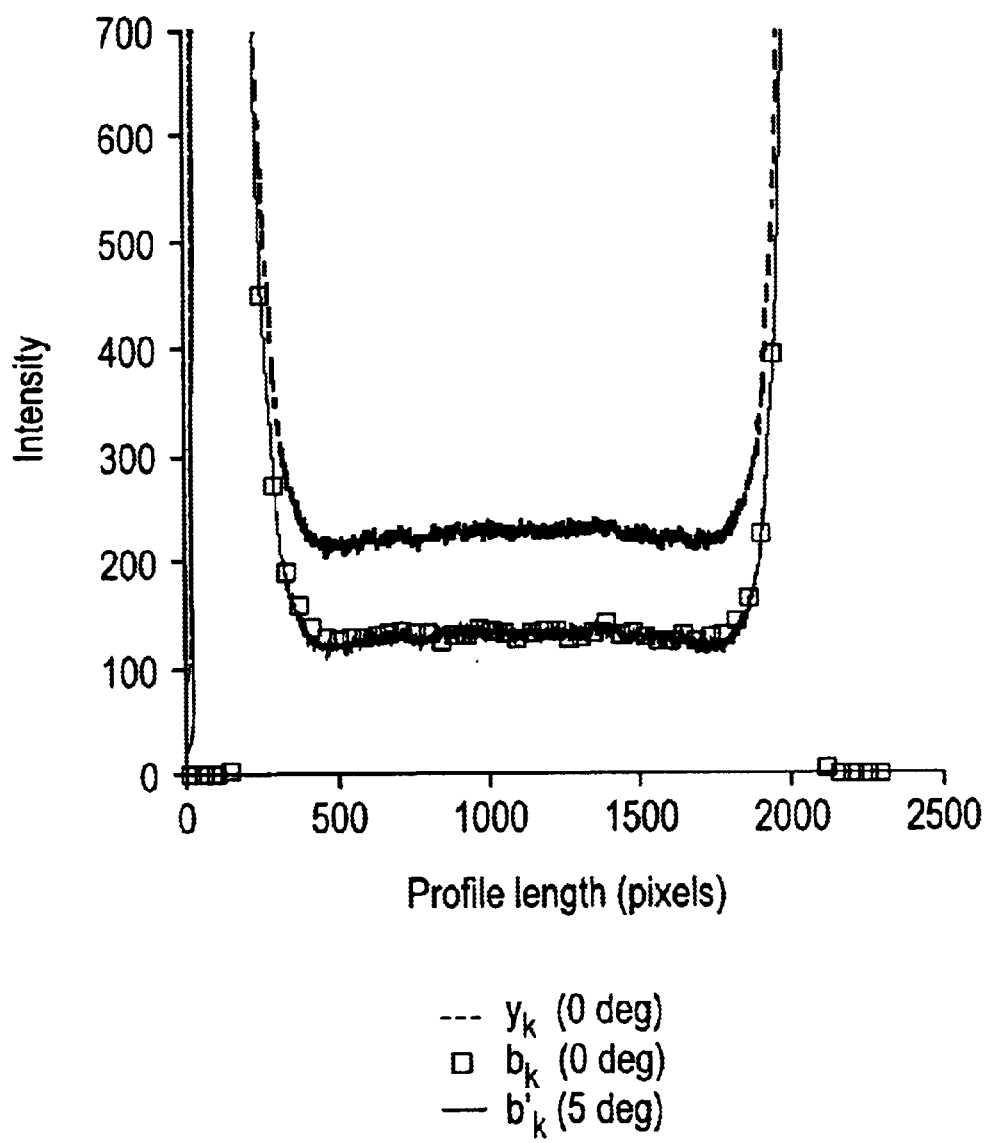

FIG. 2 is a diagram which demonstrates the various parameters in which following equations are couched. FIG. 3, on the other hand, is a schematic perspective view of an experimental arrangement which was used to conduct tests to verify the voracity of the effect of the algorithm that can implement the estimations enabled using the techniques outlined below. In this arrangement, a plurality of acrylic plates are disposed one on top of the other.

This arrangement radiologicially approximates tissue such as breast tissue and thus enables a mammographic simulation. Although not specifically indicated, the arrangement is intended to represent, merely by way of example, a compressed breast thickness, which is included along with a detector cover thickness and a compression paddle thickness. This enables a thickness value to be determined and used in calculations to determine a length of the path along which a ray has passed and which length is used in the disclosed embodiment of the scatter correction process.

Scatter Correction Model

A mammography image can be thought of as formed by unattenuated X-ray photons arriving directly from the source (direct events), plus photons that scatter into the detector from the breast and the acquisition system. The measured image y is then defined as $$y=b+s,\qquad\text{Equation 1}$$

where b represents the direct events detected and s is the image formed by x-ray photons scattered. Here, we are interested in recovering the direct image b. The term s can be modeled as a convolution between a scatter kernel p and the direct image b, so that $$s=p*b,\qquad\text{Equation 2}$$

where * is the convolution operator. The scatter kernel p can be though of as the probability that an X-ray photon directed onto pixel k of the detector will actually be scattered into pixel j.

From Equations 1 and 2 we have $$y=b+p*b.\qquad\text{Equation 3}$$

Explicitly, for any given pixel j in the experimental image, we can express Equation 3 as $$y_j = b_j + \sum_{k=1}^{N} p_{jk} b_k,$$

where the index k spans all pixels of the detector (1 through N).

Assuming that p is known for a given image acquisition system configuration and object being imaged, we can make an initial estimation of the scatter signal through the expression $$s^{(0)} = \frac{p*y}{1+\bar{p}} = \frac{p*(b+p*b)}{1+\bar{p}} = \frac{p*b*(\delta+p)}{1+\bar{p}},\qquad\text{Equation 4}$$

where δ denotes the Kronecker delta function and $\bar{p}$ is the scatter kernel norm. Rearranging Equation 1 we can write an initial estimate of the direct events $$b^{(0)}=y-s^{(0)}.\qquad\text{Equation 5}$$

The scatter corrected image can then be estimated iteratively using the expression $$b^{(n)} = \frac{y}{2^t} + \left(\frac{2^t-1}{2^t}\delta - \frac{p}{2^t}\right)*b^{(n-1)},\qquad\text{Equation 6}$$

where we must set the scatter kernel norm to $\bar{p}<2^t$ in order to insure convergence.

Scatter Kernel Asymmetry

The angular incidence of the X-ray photons introduces an asymmetry in the original scatter kernel $P_{jk}$. Originally, if the angle of incidence between the X-ray and the normal to the detector surface is zero degrees, the probability of a photon from ray k to scatter and be detected in pixel j, is assumed symmetric and spatially invariant with respect to the indices k and j, so the kernel could be written explicitly as $p_{j-k}$. Therefore the kernel p depends only on the relative distances between pixels k and j. This symmetry is readily seen in FIG. 2, where the kernel $P_{jk}=P_{jk}$. However, if the angle of incidence of the radiation is $\alpha \neq 0$, then the length of the photon path from the point of scatter is different for pixels j and j'. Consequently the probability of transmission of the X-ray photons scattered into pixels j and j' will differ and in general $P'_{j'k} \neq P'_{jk}$.

We introduce a correction factor which relates the scatter kernels at zero degrees with the angular scatter kernel so that $$P'_{jk} = N\omega_{jk} P_{jk}, \quad \text{Equation 7}$$

wherein:

$P_{jk}$ is the shape and magnitude of the scatter at zero degrees;

N is an empirically determined normalization factor; and $\omega_{jk}$ is an asymmetry factor given by $$\omega_{jk} = \frac{e^{-\mu(r'-r)}rz}{r'z'}, \quad \text{Equation 8}$$

where $\mu$ is the mean attenuation coefficient of X-ray photons in the breast tissue.

Distance r is given by $$r = \sqrt{z^2 + \rho^2}, \quad \text{Equation 9}$$

where $\rho$ the distance between pixels k and j.

The distance r' is given by $$r' = \sqrt{(\rho - z\tan\alpha)^2 + z^2}, \quad \text{Equation 10}$$

The estimated height z' (angular incidence) at which the scatter events take place are given by $$z' = \left( l'_k - \frac{\frac{1 - e^{-\mu l'_k}}{\mu}\left(l'_k + \frac{1}{\mu}\right)}{1 - e^{\mu l'_k}} \right)\cos(\alpha), \quad \text{Equation 11}$$

where $$l'_k = \frac{t}{\cos(\alpha)}, \quad \text{Equation 12}$$

and $\mu$ is the attenuation coefficient for the mean energy of the X-ray spectrum in acrylic (viz., the material used in the plates shown in FIG. 2 to emulate breast tissue).

The estimated height z (perpendicular distance) can be obtained from the expression for z' by setting $\alpha=0$.

The normalization factor N is given by $$N = \frac{1}{\sum_{jk} \frac{e^{-js(r'-r)rz}}{r'z'}} f(t, \alpha), \quad \text{Equation 13}$$

where f(t, $\alpha$) is an empirically-determined scatter-kernel normalization factor that depends on the thickness of the object imaged and the angle of the radiation source with respect to the normal of the detector plane. Equation 6 then remains $$b'^{(n)} = \frac{y}{2^l} + \left(\frac{2^l - 1}{2^l}\delta - \frac{p'}{2^l}\right) * b'^{(n-1)}. \quad \text{Equation 14}$$

Determination of the Scatter-Kernel Normalization Factor

The angular incidence of radiation introduces an asymmetry in the scatter kernel, as explained in the previous section. In addition, the magnitude of the kernel changed in a manner that was unaccounted for by the simple increase of path length $l'_k$ of photons through the imaged object as a function of $\alpha$. This introduces an empirical normalization function f(t, $\alpha$), which is determined by a series of measurements spanning object thicknesses t from 1 to 8 cm and radiation incidence angles from 0° to 45°.

Two images were taken for any given object thickness t and incident X-ray angle $\alpha$: The slit collimator image was taken as shown in FIG. 3. The slit collimator was made of a sheet of Tungsten with a thickness of 20 mils. A 1 mm wide slit allowed X-rays through. The signal directly beneath the slit is effectively scatter-free.

An open-geometry image was acquired in the same way as the slit collimator image, except that the collimator was removed, thus allowing for scatter in the image.

The scatter-free signal $b_k$ acquired in the slit-collimator image was then compared to the scatter-corrected open-geometry signal $b'_k$ by calculating the reduced chi-squared $\chi^2$ between the scatter-free and scatter-corrected signals;

$$\chi^2 = \frac{1}{N-1}\sum_{k=1}^{N}(b_k - b'_k)^2. \quad \text{Equation 15}$$

An empirical kernel normalization factor was determined by minimizing for $\chi^2$ a given t and $\alpha$. A surface function f(t, $\alpha$) was then generated by regression.

Validation Through Anthropomorphic Phantoms

Experimental data were acquired using a prototype tomosynthesis X-ray system for mammography. Three anthropomorphic breast phantoms were used for validation of the scatter-correction technique, with nominal thickness of 4, 5 and 6 cm. Their glandular/fat percent composition was 50/50, 70/30 and 80/20, respectively. A full set of projections (11 images) were acquired for slit collimator and open geometry for each phantom. Each set of projections covered tube angles ranging from +25° to −25° in 5° steps. The technique used was Rh/Rh, 32 kVp and 10 mAs per projection image.

The open-geometry projections were scatter-corrected using the new scatter kernel $P'_{jk}$, and compared to the scatter-free signal acquired using the slit collimator.

FIGS. 3–8 show the open-geometry, scatter-free and scatter corrected signals for pixels directly below collimator slit. As will be appreciated, these figures show a comparison between open-geometry ($y_k$) scatter-free ($b_k$) and scatter-corrected ($b'_k$) signals for a 25° angular acquisition. The mean difference between the scatter-free and scatter-corrected is less than ~3%.

Figure 10:
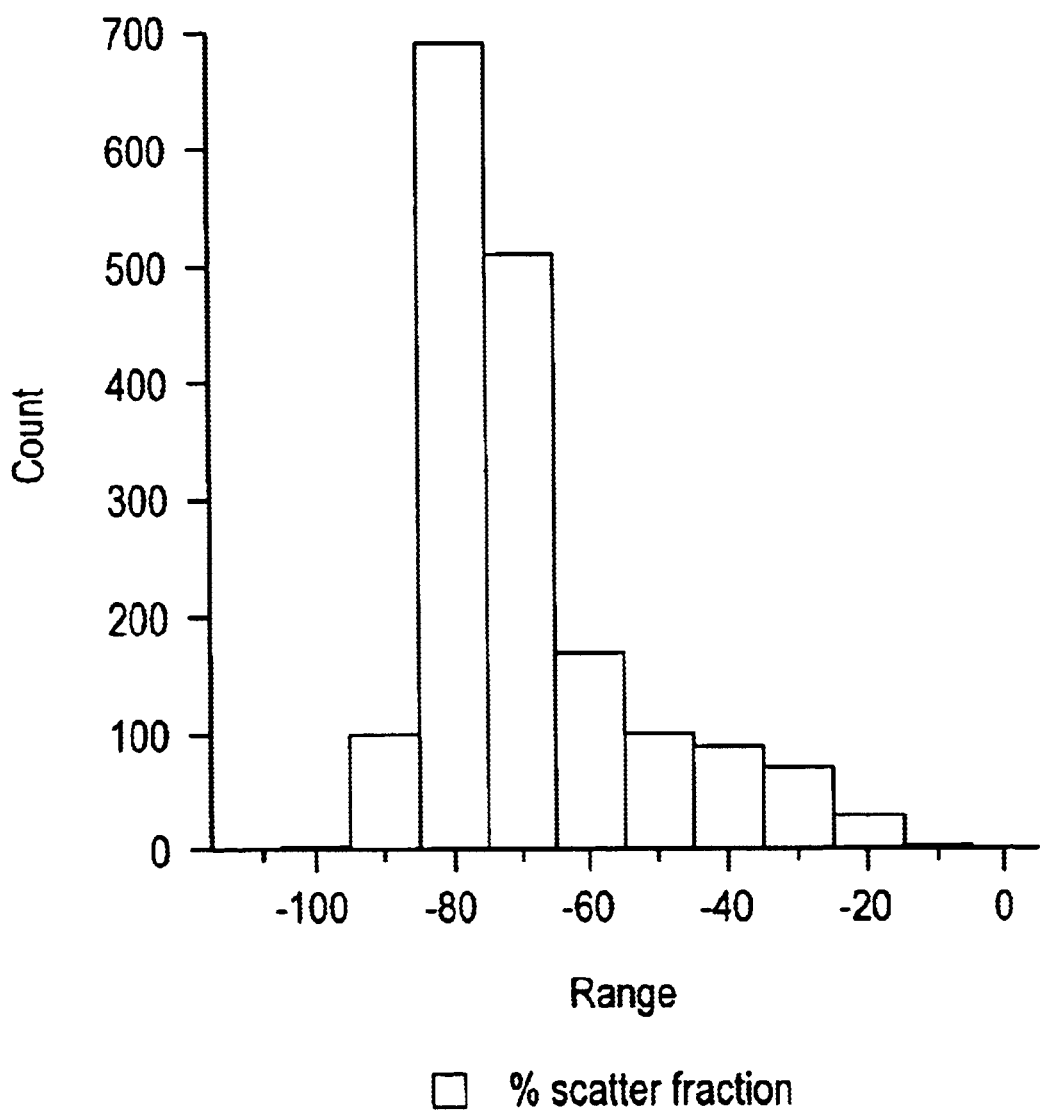
FIGS. 10 and 11 are histograms wherein the histogram of FIG. 10 shows the percent deviation between the scatter-free signal and the open geometry signal within the 5 cm breast phantom (25° acquisition)
Figure 11:
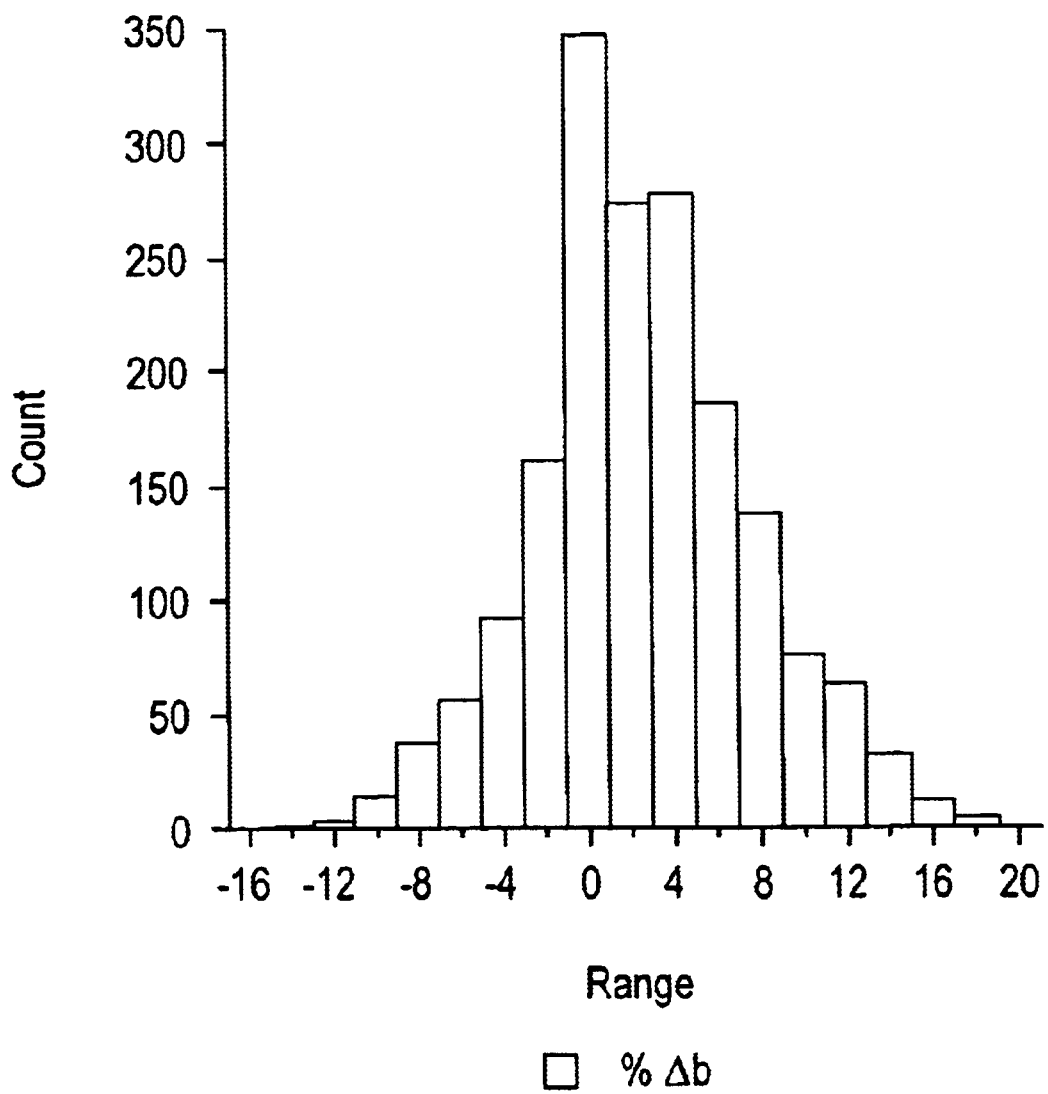

In the histogram shown in FIG. 10, the % deviation between the scatter-free signal and the open geometry signal within the 5 cm breast phantom (25° acquisition) is shown. After scatter correction the percent deviation between the scatter-free signal and the scatter corrected signal within the 5 cm breast phantom (25° acquisition) is show in the histogram of FIG. 10.

TABLE 1

| | 25 deg | | 20 deg | | 15 deg | | 10 deg | | 5 deg | | 0 deg | |
|---|---|---|---|---|---|---|---|---|---|---|---|---|
| | scatter correction | no scatter correction | scatter correction | no scatter correction | scatter correction | no scatter correction | scatter correction | no scatter correction | scatter correction | no scatter correction | scatter correction | no scatter correction |
| % bias | 0.81 | −68.64 | 3.38 | −67.16 | 2.40 | −67.26 | 1.97 | −66.63 | 1.89 | −65.86 | 1.90 | −65.40 |
| % standard deviation | 4.67 | 16.90 | 4.74 | 15.40 | 4.59 | 14.06 | 4.47 | 13.40 | 4.57 | 13.70 | 4.59 | 14.26 |

As will be appreciated, the scatter-corrected projections obtained with the present invention are comparable with the nearly scatter-free signal obtained using a slit collimator. Experimental data shows that the mean percent difference between the scatter corrected and the scatter-free projection signal is less than 3% in all cases, even in the edge region where there is rapid change in the thickness of the breast phantoms.

As will be appreciated, this table shows the bias and standard deviation of the scatter-free signal and the open-geometry signal with and without scatter correction and highlights the effectiveness of the technique.

The content of an article entitled Digital Tomosynthesis in Breast Imaging by Loren T. Niklason et al., Radiology. 205(2), 1997 p 399–406, is hereby incorporated in its entirety by reference thereto.

The content of copending U.S. patent application Ser. No. 10/062,338 (Attorney Docket No. RD 28622) entitled METHODS AND APPARATUS FOR CORRECTING SCATTER, is also incorporated by reference thereto.

While the invention has been described in connection with a tomographical examination using X-rays, it will be understood that the estimation of scatter concept on which the present invention is based, is not limited to the use of X-rays nor living tissue and can be applied to inanimate objects such as air-craft wings or the like carried out using any suitable radiation source such as a gamma or electron beam source. Further, the various modifications and changes to the embodiment of the invention disclosed will be self evident to the those skilled in the art to which the present invention pertains or mostly closely pertains, when equipped with the preceding disclosure and the need to modify and/or adapt the disclosed concept.

What is claimed is:

1. A method of estimating scatter in an image, where radiation from a radiation source is transmitted through an object to be imaged and is incident on a detector at an inclined angle, comprising the steps of:
   explicitly modeling an effect of angular incidence of the radiation on a scatter signal, including deriving, using an empirically based correction which includes the effect of an angle of incidence of the radiation on the detector, an estimate of the scatter signal in image data derived from the incident radiation on the detector.

2. A method as set forth in claim 1, further comprising the step of calibrating the scatter signal depending on an angle of incidence of radiation and a thickness of the imaged object.

3. A method as set forth in claim 1, further comprising the step of re-normalizing the scatter signal depending on an angle of incidence of radiation and a thickness of the imaged object.

4. A method as set forth in claim 1, further comprising the step of correcting scatter from the image using inverse-filtering.

5. A method as set forth in claim 1, further comprising the step of subtracting the estimate of the scatter signal from a total image derived using data based on the radiation incident on the detector, to obtain an image which is scatter corrected.

6. A method of calculating and removing scatter from an image, where radiation emitted from a source is transmitted through an imaged object, is incident on a detector at an acute angle, comprising:
   explicitly modeling the effect of angular incidence of radiation in a scatter signal;
   re-normalizing the scatter signal depending on the angle of incidence of radiation and the thickness of the object imaged; and
   correcting scatter from an image based on inverse-filtering.

7. A method of estimating scatter in an X-ray image, where radiation emitted from an X-ray source is transmitted through an imaged object and is incident on the X-ray detector at an acute angle, comprising:
   explicitly modeling the effect of angular incidence of X-ray radiation in a scatter signal; and
   calculating, via convolution, an estimate of the scatter signal in an X-ray image.

8. A method of estimating an asymmetrical scatter kernel wherein asymmetry is introduced by angular incidence of radiation, which has been emitted from a source and transmitted through an object to be imaged, on a detector, comprising:
   modifying scatter that would be derived wherein the radiation is directly incident on the detector with zero degrees of inclination, using an asymmetry factor which indicates the shape and magnitude of the scatter kernel and which varies with an angle at which the radiation is incident on the detector, a mean attenuation coefficient of the object, and a distance the radiation has traveled through the object.

9. A computer readable medium encoded with a program executable by a computer for estimating scatter in an image wherein radiation from a radiation source is transmitted through an object to be imaged and is incident on a detector at an inclined angle, said program being configured to instruct the computer to
   explicitly model an effect of angular incidence of the radiation on a scatter signal, including deriving, using an empirically based correction which includes the effect of an angle of incidence of the radiation on the detector, an estimate of the scatter signal in image data derived from the incident radiation on the detector.

10. A computer readable medium as set forth in claim 9, wherein the program is further configured to instruct the computer to calibrate the scatter signal depending on an angle of incidence of radiation and a thickness of the imaged object.

11. A computer readable medium as set forth in claim 9, wherein the program is further configured to instruct the computer to re-normalize the scatter signal depending on an angle of incidence of radiation and a thickness of the imaged object.

12. A computer readable medium as set forth in claim 9, wherein the program is further configured to instruct the computer to correct scatter from the image using inverse-filtering.

13. A computer readable medium as set forth in claim 9, wherein the program is further configured to instruct the computer to subtract the estimate of the scatter signal from a total image derived using data based on the radiation incident on the detector, and obtain an image which is scatter corrected.

14. A computer readable medium encoded with a program executable by a computer for estimating scatter in an image wherein radiation from a radiation source is transmitted through an object to be imaged and is incident on a detector at an inclined angle, said program being configured to instruct the computer to:

explicitly model the effect of angular incidence of radiation in a scatter signal;

re-normalize the scatter signal depending on the angle of incidence of radiation and the thickness of the object imaged; and correct scatter from an image based on inverse-filtering.

15. A computer readable medium encoded with a program executable by a computer for estimating scatter in an image wherein radiation from a radiation source is transmitted through an object to be imaged and is incident on a detector at an inclined angle, said program being configured to instruct the computer to:

explicitly model the effect of angular incidence of X-ray radiation in a scatter signal; and calculate, via convolution, an estimate of the scatter signal in an X-ray image.

16. A computer readable medium encoded with a program executable by a computer for estimating scatter in an image wherein radiation from a radiation source is transmitted through an object to be imaged and is incident on a detector at an inclined angle, said program being configured to instruct the computer to modify scatter that would be derived wherein the radiation is directly incident on the detector with zero degrees of inclination, using an asymmetry factor which indicates the shape and magnitude of the scatter kernel and which varies with an angle at which the radiation is incident on the detector, a mean attenuation coefficient of the object, and a distance the radiation has traveled through the object.

17. An imaging system comprising:

a radiation source and a detector array, wherein the radiation source and the detector array are movable relative to one another;

a computer coupled to the detector array and the radiation source and configured to estimate scatter in an image wherein radiation from a radiation source is transmitted through an object to be imaged and is incident on a detector at an inclined angle, by explicitly modeling an effect of angular incidence of the radiation on a scatter signal, including deriving, using an empirically based correction which includes the effect of an angle of incidence of the radiation on the detector, an estimate of the scatter signal in image data derived from the incident radiation on the detector.

18. An imaging system as set forth in claim 17, wherein the computer is further configured to calibrate the scatter signal depending on an angle of incidence of radiation and a thickness of the imaged object.

19. An imaging system as set forth in claim 17, wherein the computer is further configured to re-normalize the scatter signal depending on an angle of incidence of radiation and a thickness of the imaged object.

20. An imaging system as set forth in claim 17, wherein the computer is further configured to correct scatter from the image using inverse-filtering.

21. An imaging system as set forth in claim 17, wherein the computer is further configured to subtract the estimate of the scatter signal from a total image derived using data based on the radiation incident on the detector, and obtain an image which is scatter corrected.

22. An imaging system for estimating scatter in an image wherein radiation from a radiation source is transmitted through an object to be imaged and is incident on a detector at an inclined angle, said system including a computer configured to:

explicitly model the effect of angular incidence of radiation in a scatter signal;

re-normalize the scatter signal depending on the angle of incidence of radiation and the thickness of the object imaged; and correct scatter from an image based on inverse-filtering.

23. An imaging system for estimating scatter in an image wherein radiation from a radiation source is transmitted through an object to be imaged and is incident on a detector at an inclined angle, said system including a computer configured to:

explicitly model the effect of angular incidence of X-ray radiation in a scatter signal; and calculate, via convolution, an estimate of the scatter signal in an X-ray image.

24. An imaging system for correcting asymmetrical scatter in an image wherein radiation from a radiation source is transmitted through an object to be imaged and is incident on a detector at an inclined angle, said system including a computer configured to:

to modify scatter that would be derived wherein the radiation is directly incident on the detector with zero degrees of inclination, using an asymmetry factor which indicates the shape and magnitude of the scatter kernel and which varies with an angle at which the radiation is incident on the detector, a mean attenuation coefficient of the object, and a distance the radiation has traveled through the object.

* * * * *